Figure 1:
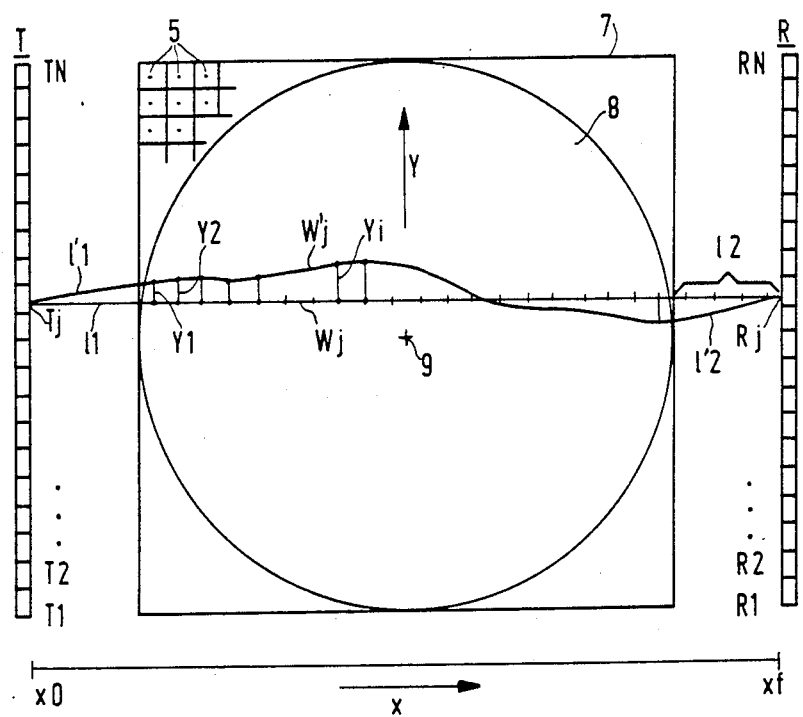

United States Patent [19]

McKinnon

[11] Patent Number: 4,669,311
[45] Date of Patent: Jun. 2, 1987

[54] METHOD OF DETERMINING AN ACOUSTIC REFRACTIVE INDEX DISTRIBUTION IN AN EXAMINATION ZONE, AND DEVICE FOR PERFORMING THE METHOD

[75] Inventor: Graeme-Colin McKinnon, Ellerau, Fed. Rep. of Germany

[73] Assignee: U.S. Philips Corporation, New York, N.Y.

[21] Appl. No.: 830,315

[22] Filed: Feb. 18, 1986

[30] Foreign Application Priority Data

Feb. 20, 1985 [DE] Fed. Rep. of Germany ....... 3505764

[51] Int. Cl.$^4$ ............................................. G01N 29/04
[52] U.S. Cl. ........................................ 73/598; 73/602; 73/626; 128/660

[58] Field of Search ................. 73/598, 602, 618, 626; 128/660

[56] References Cited

U.S. PATENT DOCUMENTS 4,279,157 7/1981 Schomberg et al. ................. 73/618
4,594,662 6/1986 Devaney ............................... 73/602
4,598,366 7/1986 Devaney ............................... 73/602

Primary Examiner—Anthony V. Ciarlante
Attorney, Agent, or Firm—Jack E. Haken

[57] ABSTRACT

A method and device for determining the internal structure of the body by means of ultrasound beams from transit time measurement. An iterative solution of integral equations is used to calculate the actual path which the ultrasound beams follow through the object.

4 Claims, 7 Drawing Figures

METHOD OF DETERMINING AN ACOUSTIC REFRACTIVE INDEX DISTRIBUTION IN AN EXAMINATION ZONE, AND DEVICE FOR PERFORMING THE METHOD

The invention relates to a method of determining the internal structure of a body by means of a plurality of ultrasound beams which traverse the body in different directions from one or more transmitter elements of an ultrasound transmitter device in order to be converted into electric signals by one or more receiver elements of an ultrasound receiver device. The transit times of the ultrasound beams are measured. The approximate path of each ultrasound beam is determined at least once from the transit times and a predetermined acoustic refractive index distribution which approximates the structure of the body in order to calculate its transit time. Data is then derived from the measured and the calculated transit time of the ultrasound beams for a step-wise correction of the acoustic refractive index distribution. The invention also relates to a device for performing this method.

Such a method and device are known from U.S. Pat. No. 4,279,157. The calculation method, moreover, is described in detail in H. Schomberg "Nonlinear image reconstruction from projections of ultrasonic travel times and electric current densities", Mathematical aspects of computerized tomography Proceeding (Oberwolfach 1980, editors G. T. Herman and F. Natterer), Springer-Verlag, pages 270–291. The advantage of the known method is that the calculation of the acoustic refractive index distribution is not based on the assumption that the sound propagates along rectilinear paths in the body. Because the acoustic refractive index in a real body varies as a function of location, the path of the ultrasound wave does not extend rectilinearly through the body, so that an acoustic refractive index distribution derived on the basis of the above assumption will be necessarily false.

According to the known method, the problem imposed by the usually non-linear path of the ultrasound beam through the examination zone or the body being examined is solved by means of a set of coupled first-order differential equations and the secondary condition that the ultrasound beam must depart from the ultrasound transmitter location and terminate at the ultrasound receiver location. Starting from the location of the transmitter, an initial direction is first imposed until a next image point is reached. For the next image point a new direction towards the next image point is calculated on the basis of the differential equation and so on, so that a path is obtained whose direction varies step-wise. However, this path usually does not reach the ultrasound receiver location a correction can be derived from the initial direction of the ultrasound beam, from the distance between the ultrasound receiver location and the ultrasound beam path a correction can be derived for the initial direction of the ultrasound beam, after which the method is performed again. These calculation cycles are repeated until the ultrasound receiver location is at least approximately reached. It will be apparent that this calculation method is very complex and time consuming.

It is an object of the invention to provide a method of determining the path of the ultrasound beam through the examination zone such that the path determined always connects the ultrasound transmitter location to the ultrasound receiver location. The integral equations $$Y = \int_{xO}^{x} \frac{w}{n} \int_{xO}^{s} gw\,dt\,ds + A \int_{xO}^{xf} \frac{w}{n} ds \quad (1)$$

and $$Z = \int_{xO}^{x} \frac{w}{n} \int_{xO}^{s} hw\,dt\,ds + B \int_{xO}^{x} \frac{w}{n} ds \quad (2)$$

are solved, in which x, t, s denote the direction of the straight connecting lines between the ultrasound transmitter location $xO$ and the ultrasound receiver location $xf$; Y and Z denote the distance between the path and this straight line in two mutually perpendicular directions; n denotes the acoustic refractive index; g and h denote the gradients thereof in the y and the z direction, respectively; w denotes the derivative of the path with respect to x, and A and B are factors which are chosen so that the conditions $Y(xf)=0$ and $Z(xf)=0$ are satisfied.

In these equations the factors A and B are separately selected for each path so that Y and Z are zero at the location xf, which means that the path determined terminates at the ultrasound receiver location. This is always the case when the following relations hold good:

$$A = - \frac{\int_{xO}^{xf} \frac{w}{n} \int_{xO}^{s} gw\,dt\,ds}{\int_{xO}^{xf} \frac{w}{n} ds} \quad (3)$$

$$B = - \frac{\int_{xO}^{xf} \frac{w}{t} \int_{xO}^{xf} hw\,dt\,ds}{\int_{xO}^{xf} \frac{w}{n} ds} \quad (4)$$

These equations can be very simply solved by means of a digital computer.

It can be demonstrated that the integral over the refractive index on the path thus determined is substantially a minimum value with respect to the integrals over the other paths feasible between the two points. The path thus calculated, therefore, at least suitably approximates the path which would be taken by an ultrasound beam through an examination zone in which the underlying refractive index distribution is given. The fact that the calculated path does not correspond exactly to the actual path is due to the fact that the location-dependent variables n, g, h, w over which integration takes place in accordance with the equations (1) and (2) initially are not known for the calculated points Y and Z. The value of these parameters on the path can be determined only when the path is known, so that a new path can be calculated therefrom. Therefore, in a version of the method in accordance with the invention the path is iteratively solved by determining the values n, g and h for the coordinates of the path determined during a preceding cycle.

It may be that the actual path of the ultrasound beam is situated, at least over parts of its length, between a first calculated path and a second calculated path whose calculation is based on the calculation of the first path.

This means that for the relevant parts of the path the coordinates of the first path were too small (or too large) and the coordinates of the second path were too large (or too small). This "overshoot" or "oscillation" of the solutions found can be avoided in a further version in accordance with the invention in the coordinates Yn, Zn of the new path are calculated in accordance with the equations $$Yn = dYa + (d-1)Y \quad (5)$$

$$Zn = dZa + (d-1)Z \quad (6)$$

in which d is a predetermined factor which satisfies $0 < d < 1$. from the newly calculated coordinates Y, Z and the coordinates Ya, Za applicable thus far for the same x value.

A device for performing the method comprises an ultrasound transmitter which consists of a plurality of transmitter elements, a separate ultrasound receiver which consists of a plurality of receiver elements, means for selecting transmitter and receiver elements in such a manner that the activated transmitter and receiver elements are always situated on parallel, straight connecting lines, means for measuring the transit time of the ultrasound beams between the relevant activated transmitter and receiver elements, and an arithmetic device for determining the refractive index distribution in an examination zone situated between the ultrasound transmitter device and the ultrasound receiver device. The arithmetic device includes means for calculating, using an integral equation, the distance between the ultrasound beam and the associated straight connecting line in a plurality of points.

Figure 7:
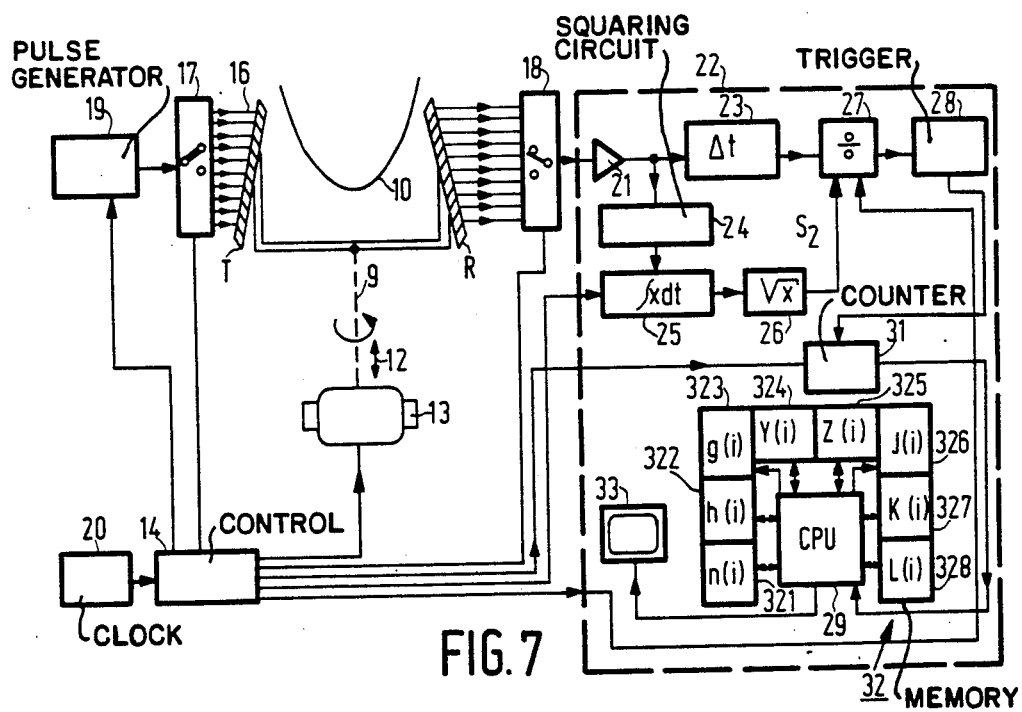
Figure 2:
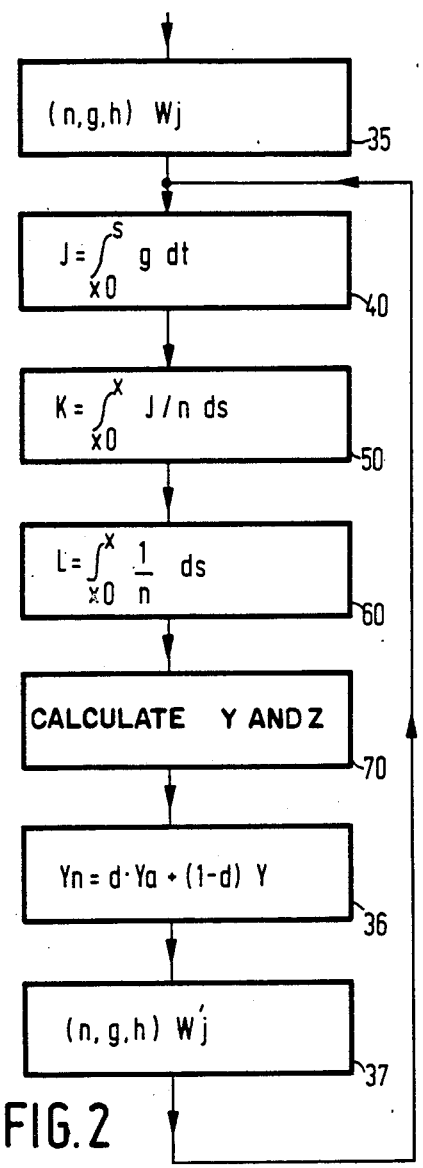

The invention will be described in detail hereinafter with reference to the drawing. Therein:

FIG. 1 diagrammatically shows an ultrasound transmitter and receiver device and the examination zone which is situate therebetween, FIG. 2 shows the succession of calculation steps for determining the Y coordinate of the path of the ultrasound beam, FIGS. 3 to 6 show flowcharts illustrating different subroutines for performing individual calculation steps as shown in FIG. 2, and FIG. 7 diagrammatically illustrates a device for performing the method in accordance with the invention.

The reference T in FIG. 1 denotes an ultrasound transmitter device and the reference R denotes an ultrasound receiver device. The ultrasound transmitter device consists of a row of N transmitter elements T1 ... TN. Similarly, the ultrasound receiver device R consists of N receiver elements R1 ... RN. A suitable value of N is 64. The resolution can be improved or a larger examination zone can be covered, when use is made of a larger number of transmitter and receiver elements but the complexity then also increases. The distance between the two parallel rows T and R is larger than the length of the rows. The devices T and R are accommodated in a tank (not shown) which is filled with water or another suitable liquid and are rotatable about the axis 9 which extends vertically with respect to the plane of drawing) by means of a motor drive (not shown). The examination zone which the acoustic refractive index distribution can be determined is situated between the rows T and R and and is bounded by the circular cylinder 8 whose axis coincides with the axis of rotation 9.

An electronic control circuit (not shown) switches the transmitter and receiver elements in such a manner that always that receiver element is activated for reception which is situated, together with the transmitter element transmitting at the relevant instant, on a straight connecting line which extends parallel to the x direction, so that for example the elements T1, R1; T2, R2; ... Tj, Rj are activated together. The ultrasound energy which is generated, for example by the ultrasound transmitter element Tj reaches the associated receiver element Rj along a path W'j which usually deviates from the straight connecting line Wj between the two elements. For each of these ultrasound paths the transit time is measured; when this operation has been performed for all N pairs, the ultrasound converter device T, R is rotated through an angle, for example 360°/N, after which the same measurement cycle is repeated. The rotation and the subsequent measurement cycle are performed N times. These measurements are repeated for other layers, the ultrasound converter devices T and R then being relatively displaced with respect to the examination zone in the z direction, i.e. perpendicularly to the plane of drawing.

Subsequently, the acoustic refractive index distribution in the examination zone 8 is reconstructed. To this end, on the basis of a predetermined distribution which approximates the anticipated refractive index distribution the paths W'j are determined for each pair (for example Tj, Rj), for each of said directions and for each layer. A correction value is calculated from the comparison between the calculated transit time, being the path integral of the refractive index, and the measured transit time and the acoustic refractive indices along the calculated path W'j and inside the cylinder 8 are corrected so that the calculated transit time corresponds to the measured transit time. This is repeated for each of the pairs T1, R1 ... TN, RN, for each direction and for each layer. Thus, a refractive index distribution is obtained which already corresponds better to the actual refractive index distribution than the preceding one, and which itself can be further improved by further iteration cycles.

The method described thus far is essentially known from the previously referenced publications which are incorporated herein by reference. The invention differs from the known method in respect of the determination of the paths W'j for the ultrasound beams; this operation is the most complex part of the entire iteration operation. This method will be described in detail hereinafter with reference to FIG. 2.

The procedure is started (block 35) with an approximate distribution of the parameters n, g, h. Therein, n is the acoustic refractive index at the relevant location, and the following holds good for g and h $$g = \frac{\partial n}{\partial y} \quad (7)$$

$$h = \frac{\partial n}{\partial z}. \quad (8)$$

The value w must also be present per se, satisfying the equation $$w = \left(1 + \left(\frac{dy}{dx}\right)^2 + \left(\frac{dZ}{dx}\right)^2\right)^{\frac{1}{2}} \quad (9)$$

but this value is assumed to be 1 for the entire zone. This substantially facilitates the calculation and introduces only a slight error, because w is approximately 1 for the major practical cases, for example for mammography.

It is not sufficient to know these parameters for a flat zone because the ultrasound beam does not propagate rectilinearly in the examination zone. On the contrary, they must rather be known for a three-dimensional zone. Therefore, a memory in which the parameters n, g, h are stored for each volume element (referred to hereinafter as voxel). All voxels must be provided together form a cubic space 7, whose cross-section in the plane of drawing of FIG. 1 forms a square having sides whose length corresponds to the diameter of the cylinder 8 and which consists of N×N voxels, some of which are denoted by the reference numeral 5 in FIG. 1.

The approximate distribution of n, g and h used for the reconstruction can be arbitrary per se; however, the better the initial distribution corresponds to the actual refractive index distribution, the less complicated the calculation will be. Therefore, a refractive index distribution for which the same values n as well as g=0 and h=0 are stored for all voxels, would be comparatively unattractive. A better approximate distribution is obtained when it is first assumed that the ultrasound beam propagates rectilinearly and when from the measured transit time, which corresponds to the path integral of the refractive index, the refractive index distribution is reconstructed in the same way as in computer tomography where the distribution of the absorption coefficients is determined from the measured absorption values which correspond to the path integral over the absorption coefficients. From this refractive index the differential quotients g and h can be calculated as a difference quotient.

During the next step (block 40), the integral J is determined which corresponds to the inner integral in the double integral of the equation (1) when w is assumed to be equal to 1.

Using the values J thus determined, the integral K which corresponds to the double integral of the equation (1) is determined (block 50) w again being assumed to be equal to 1. Finally, the integral L is calculated (block 60) which corresponds to the second integral in the equation (1) for w=1. Using the values J, K and L thus calculated, the y coordinates can be calculated in accordance with the equation (1) (block 70). Analogously the Z values are calculated. For the latter operation it is merely necessary to replace the parameter g by h in block 40.

The coordinates Y and Z thus found can in principle be considered to be coordinates of the new path. However, it appears that these coordinates are usually situated away from the actual path when the path Wj is considered. However, this "overshoot" or "oscillation" in the calculation of the path of the ultrasound beam through the examination zone can be avoided or reduced when the coordinates for the new path are calculated in accordance with the equation (5). Therein, Yn is the value of the y coordinate for the new path, Y is the previously calculated (block 70) Y value and Ya is the y coordinate of the path Wj thus far at the same location x; d is an attenuation factor which is smaller than 1 and larger than 0. The smaller this value, the more the "overshoot" or "oscillation" will be; the more this value approximates 1, the more this "overshoot" or "oscillation" will be suppressed, but the more often it will also be necessary to calculate the path in an iterative manner in order to ensure that the path found by calculation indeed corresponds to the actual path. Analogously, the z coordinates for the new path are determined in accordance with the equation (6). The calculated path generally does not exactly correspond to the path which would be followed by the ultrasound beam for the given refractive index distribution; this is not only because of the manipulation in block 36, but also because the equations (1) and (2) exactly represent the coordinates of the actual path only if the parameters g, h, n w in the equations (1) and (2) correspond to the respective actual parameters on this path, i.e. at the location x, Y, Z. However, because the path or the coordinates Y and Z are in principle unknown, the parameters g, h, n, w will generally not satisfy these conditions. However, the calculated path can be iteratively made to approximate the path which would actually be followed by an ultrasound beam for the assumed refractive index distribution. To this end, the parameters n, g, h are determined again on the previously calculated path W'j. Because the path W'j usually does not extend exactly through the centres of the individual voxels, the parameters n, g, h must be determined by interpolation of the values stored for the voxels between the centres of which this path extends (block 37). Using the values thus found, the path can be calculated again (blocks 40, 50, 60, 70, 36 and 37); in comparison with the previously found path, the path thus found usually corresponds better to the path which would be followed by an ultrasound beam for the predetermined refractive index, distribution.

The diagram of FIG. 2 illustrates the calculation of the path for only a single direction of the ultrasound converter device T, R with respect to the examination zone 8 and only for a single pair of elements Tj, Rj. The calculations of the other paths, however, are independent of the calculation of the path Wj so that they can be performed independently, i.e. in parallel in time. The integral calculation in the blocks 40 and 60 can also be independently performed and the sub-integrals calculated in block 40 can be processed immediately thereafter in block 50.

Figure 3:
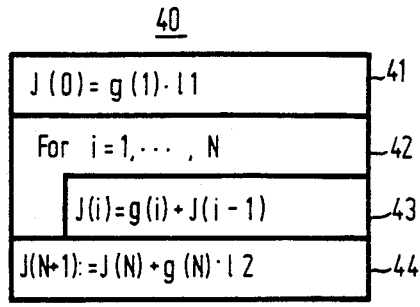

FIG. 3 is a detailed flowchart (Nassi-Schneiderman-diagram) of the steps performed during the calculation of the integral J (block 40). First the value J(o) is determined. This value would be 0 if the ultrasound transmitter device T were to coincide with the edge of the zone 7 for the individual voxels of which the values n, g and h are stored. However, because at XO the ultrasound transmitter device is situated at a distance l1 from this zone 7, this initial value is determined according to the equation $$J(o) = g(1)/l \quad (10)$$

in which l1 is the distance between the zone 7 and the ultrasound transmitter device T and g(1) is the value at the first voxel which is intersected by the straight connecting line Wj between the transmitter element Tj and the receiver element Rj. Subsequently, for all N voxels on the path Wj the integral values J(i) are calculated in accordance with the equation $$J(1) = g(i) + J(i-1) \quad (11)$$

(steps 42, 43). The value J for the $i^{th}$ voxel on the path Wj then equals the sum of the value g for this voxel and the value J for the preceding voxel (i−1). When this operation has been performed for all N voxels, the product g(N)l2 is added to the last value J(N) found, so that the fact is taken into account that the row R of receiver elements is situated at the distance l2 from the zone 7 (step 44).

The values J(i) for the values i=1,... N represent the numerical value of the integral at the locations x(1) ... x(N),x() representing the respective x value in the centre of the voxel (). The value J(N+1) corresponds to this integral at the location $x=xf$, i.e. at the location of the receiver element Rj.

Figure 4:
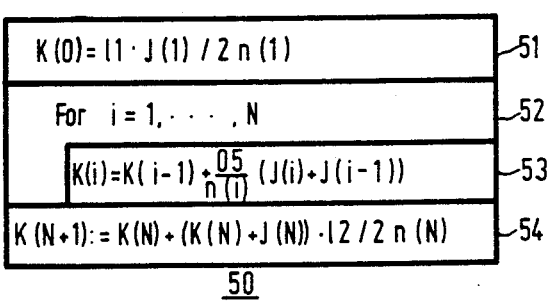

The values thus found are processed in block 50, the processing steps of which are shown in FIG. 4. The numerical integral K(i) for the $i^{th}$ voxel is again calculated (step 53) from the sumof the numeral integral K(i−1) for the preceding point (i−1) and the arithmetical mean value of the integrals J(i), J(i−-1) divided by the refractive index n(i) for this voxel. For the initial value K(o) it holds good that $$K(o) = l1 + J(1)/2n(1) \quad (12)$$

and for the value K(N+1) at the location $x=xf$ the following equation is applicable:

$$K(N+1) = K(N) + (K(N) + J(N))l2/2n(N)) \quad (13)$$

Figure 5:
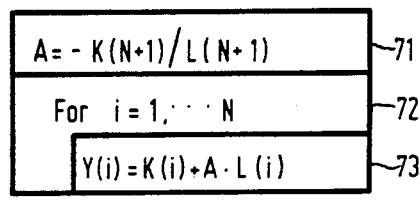

FIG. 5 shows the flowchart for the block 60 which comprises the steps 61, 62, 63 and 64 which deviate from the steps 41 42, 43 and 44 merely in that the parameter g(i) is replaced by 1/N(i).

Figure 6:
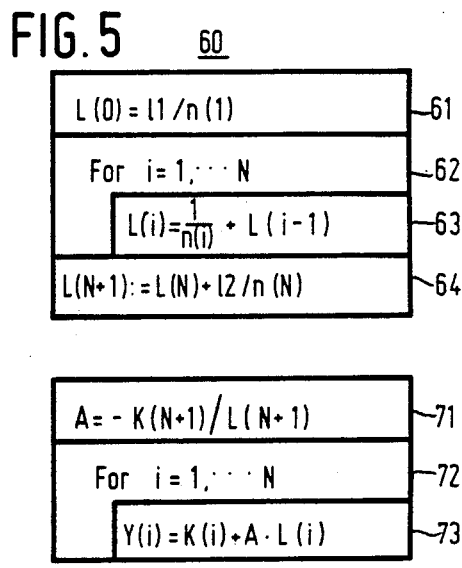

FIG. 6 shows the flowchart for the calculation of the values Y from the values K and L. In step 71 first the value A is calculated in accordance with the equation (3) as a negative quotient of the values K(N+1) and L(N+1). Subsequently (steps 72 and 73), for i=1... N the values Y(i) associated with the values x(i) are calculated in accordance with the relation $$Y(i) = K(i) + AL(i) \quad (14)$$

The calculation of the values Z(i), which can be performed independently of the calculation of the value Y(i) i.e. in parallel in time, takes place in the same way. It is merely necessary to replace g(i) by h(i) in block 40.

As has already been explained with reference to FIG. 2, subsequently Yn and Zn are calculated in accordance with the equations (5) and (6), followed by the determination of the parameters n, g, h for the newly found path W'j at the points x(i), Y(i) and Z(i), after which the blocks 40 ... 37 can be executed again. Usually between two and six interation operations must be performed. When the number of iteration operations is less than two, the calculation will be too inaccurate and in the case of more than six interation operations, hardly any further improvement will be achieved.

For the calculation it is advantageous to assume a constant value for the refractive index at all positions outside the volume 7 and at the voxels at the edge of this volume, for example at the first and the $N^{th}$ voxel on the path Wj, said constant refractive indexvalue corresponding to that of the liquid surrounding the examination zone. In that case the calculation steps 41 and 44 in FIG. 3 can be dispensed with because g(1)=g(N)= 0 and J(N+1)=J(N).

For the calculation of the integrals J, K and L for which the values g, k, n along the new path W'j are used, it is to be noted that l1 or l2 may also vary when Y(1) or Z(1) or Y(N) and Z(N) deviate from zero. In that case the values l'$_1$ and l'$_2$ (see FIG. 1) must be used in the blocks 41, 44, 51, 54 and 61, 64 instead of l1 and l2, respectively; these values l'$_1$ and l'$_2$ can be determined in accordance with Pythagoras theorem.

FIG. 7 shows a device for performing the method in accordance with the invention. A tank (not shown) for accommodating an object to be examined, for example a female breast 10, is filled with water and encloses an ultrasound transmitter device T and an ultrasound receiver device R which consist of individual ultrasound transmitter elements and receiver elements which are arranged in rows. The ultrasound transmitter device is rigidly connected to the ultrasound receiver device via the tank or another suitable support, both devices being rotatable about a central axis of rotation 9 by means of a motor 13. The elements of the ultrasound transmitter device are connected to a pulse generator 19 via a demultiplexer 17, and the elements of the ultrasound receiver device R are connected to an evaluation unit 22 via a multiplexer 18. A control unit 14 which is connected to a clock generator 20 ensures that the associated transmitter and receiver elements, for example Tj, Rj (see FIG. 1) are simultaneously activated.

For examination of another layer of the object 10 by means of the device is arranged to be displaceable in the direction of the arrow 12, i.e. in the direction of the axis of rotation 9. This mechanical displacement, however, can be dispensed with when each of the two devices T and R comprises a flat matrix of elements, a plurality of elements thereof being offset with respect to one another in the direction of the arrow 12.

In the evaluation unit 22 the output signal of the multiplexer 18 is amplified by an amplifier 21 and applied to a divider circuit 27 via a delay member 23. In the divider circuit 27 this signal is divided by a signal which corresponds to the intensity of the ultrasound signal and which is obtained by means of a squaring circuit 24 which is connected to the output of the amplifier 21 and which is coupled, via an integration circuit 25 and an evolution circuit 26, to the input of divider circuit so that the variation in the time of the output signal of the divider circuit 27 is substantially independent of the intensity of the ultrasound signals received. The output signal of the divider circuit 27 is applied to a trigger circuit 28 which stops a counter 31 when the level of the output signal exceeds a predetermined value. The number of pulses from the control unit 14 counted thus far by the counter 31 is then a measure for the transit time; however, the transit time can alternatively be determined as described in German Pat. No. 32 42 284.

The measured transit times are applied to a processing unit which includes a digital computer 29 and a memory 32. Only the parts of the memory which are important for determining the path are shown in the drawing. The memory includes sections 321, 322 and 323 in which the parameters n, g and h for a single direction and all paths Wj whose lines extend in this direction are stored. The memory also includes sections 324 and 325 in which the coordinates of the paths Y(i) and Z(i) calculated therefrom are stored and sections 326, 327 and 328 in which the values J(i) and K(i) L(i) are stored each time for a single path only. The digital computer 29 is programmed so that it can perform the calculations described with reference to the FIGS. 1 to 6.

What is claimed is:

1. In a method for determining the internal structure of a body which comprises the steps of:

transmitting pulsed energy in a plurality of ultrasound beams which traverse the body in different directions from one or more transmitter elements;

converting energy which has traversed the body in said beams into electrical signals with one or more receiver elements;

measuring the transit time of the energy in the beams through the body;

calculating the approximate path of each ultrasound beam through the body from the measured transit times the positions of the associated transmitter and receiver elements;

and calculating the spatial distribution of the acoustic refractive index in the body from a comparison of the measured transit times with transit times calculated along the approximated beam paths;

the improvement wherein, the approximate path (W'j) of each ultrasound beam is calculated using the integral equations:

$$Y = \int_{xO}^{x} \frac{w}{n} \int_{xO}^{s} gw\, dt\, ds + A \int_{xO}^{xf} \frac{w}{n} ds \quad (1)$$

and $$Z = \int_{xO}^{x} \frac{w}{n} \int_{xO}^{s} hw\, dt\, ds + B \int_{xO}^{x} \frac{w}{n} ds \quad (2)$$

in which:

x, t, and s denote the direction of straight connecting line betwen the location, xO of the ultrasound transmitter element and the location, xf, of the ultrasound receiver element which respectively transmitted and received the beam;

Y and Z denote the distance between the calculated approximate path and said straight line in perpendicular directions y and z;

n denotes the local refractive index;

g and h denote the local gradient of the refractive index in the y and z directions respectively;

w denotes the derivative of the path (W'j) with respect to x; and

A and B are factors which are chosen so that $Y(xf)=0$ and $Z(xf)=0$.

2. A method as claimed in claim 1 wherein the path (W'j) is iteratively determined by calculating values of n, g and h for points on a path determined during a previous iteration.

3. A method as claimed in claim 1 or 2 wherein coordinates, $Y_n$ and $Z_n$, along a path are iteratively calculated from coordinates along a previously calculated path, $Y_a$ and $Z_a$, using the equations:

$$Y_n = dY_a + (d-1)Y$$

$$Z_n = dZ_a + (d-1)Z$$

in which $0 < d < 1$.

4. Apparatus for determining the internal structure of a body comprising means for transmitting pulses of ultrasound energy through the body from a plurality of transmitter locations;

means for receiving said energy which has traversed the body at a plurality of receiver locations whereby said energy is transmitted through the body along a plurality of separate beam paths which connect said transmitter locations to said receiver location; and means which iteratively calculate a distribution of the acoustic refractive index within the body from the values of said measured transit times;

wherein said means which calculate the distribution include means which calculate the approximate path (W'j) along which said energy propagates from a transmitter location to a receiver location using the integral equations:

$$Y = \int_{xO}^{x} \frac{w}{n} \int_{xO}^{s} gw\, dt\, ds + A \int_{xO}^{xf} \frac{w}{n} ds \quad (1)$$

and $$Z = \int_{xO}^{x} \frac{w}{n} \int_{xO}^{s} hw\, dt\, ds + B \int_{xO}^{x} \frac{w}{n} ds \quad (2)$$

in which:

x, t, and s denote the direction of straight connecting line between the transmitter location, xO and the receiver location, xf;

Y and Z denote the distance between the calculated approximate path and said straight line in perpendicular directions y and z;

n denotes the local refractive index;

g and h denote the gradient of the local refractive index in the y and z directions respectively;

w denotes the derivative of the path (W'j) with respect to x; and

A and B are factors which are chosen so that $Y(xf)=0$ and $Z(xf)=0$.

* * * * *

UNITED STATES PATENT AND TRADEMARK OFFICE
CERTIFICATE OF CORRECTION

PATENT NO. : 4,669,311

DATED : June 2, 1987

INVENTOR(S) : GRAEME-COLIN MC KINNON

It is certified that error appears in the above-identified patent and that said Letters Patent is hereby corrected as shown below:

In the Claims:

Claim 4, line 13, delete "said".

Signed and Sealed this

Twentieth Day of October, 1987

Attest:

DONALD J. QUIGG

*Attesting Officer*  *Commissioner of Patents and Trademarks*